(12) United States Patent
Vogt

(10) Patent No.: US 10,518,232 B2
(45) Date of Patent: Dec. 31, 2019

(54) DEVICE AND METHOD FOR MANUALLY OPENING GLASS AMPULES AND A CEMENTING DEVICE

(71) Applicant: Heraeus Medical GmbH, Wehrheim (DE)

(72) Inventor: Sebastian Vogt, Erfurt (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 538 days.

(21) Appl. No.: 15/273,956

(22) Filed: Sep. 23, 2016

(65) Prior Publication Data
US 2017/0087527 A1 Mar. 30, 2017

(30) Foreign Application Priority Data
Sep. 25, 2015 (DE) .................. 10 2015 116 245

(51) Int. Cl.
*B01F 15/02* (2006.01)
*B01F 3/12* (2006.01)
(Continued)

(52) U.S. Cl.
CPC ...... *B01F 15/0206* (2013.01); *A61B 17/8833* (2013.01); *B01F 3/1207* (2013.01);
(Continued)

(58) Field of Classification Search
CPC ............ B01F 15/0206; B01F 15/0205; B05C 17/00583; B05C 17/00586; B65D 35/28;
(Continued)

(56) References Cited

U.S. PATENT DOCUMENTS

| 3,603,484 A | 9/1971 | Ogle |
| 5,551,778 A | 9/1996 | Hauke et al. |

(Continued)

FOREIGN PATENT DOCUMENTS

| DE | 313 303 C | 7/1919 |
| DE | 2921565 A1 | 12/1980 |

(Continued)

OTHER PUBLICATIONS

Australian Office Action corresponding to Australian Application No. 2016228172 dated Apr. 6, 2017.

(Continued)

*Primary Examiner* — Tony G Soohoo
*Assistant Examiner* — Elizabeth Insler
(74) *Attorney, Agent, or Firm* — Norris McLaughlin, P.A.

(57) ABSTRACT

Devices and methods manually open glass ampules within the devices. One device may include a holder having at least one deformable side wall, a supporting element, and at least one strainer/filter arranged below the holder so that the content of the opened glass ampule may flows therethrough. A first lever of the device may pivot around a first axis and a free end of the first lever may be pressed against the deformable side wall of the holder. A second lever of the device may pivot around a second axis that may divide the second lever into a short lever arm and a long lever arm. The short lever arm may be pressed against the first lever and a glass ampule may be broken open by pressure of the free end of the first lever.

20 Claims, 5 Drawing Sheets

Figure 1:
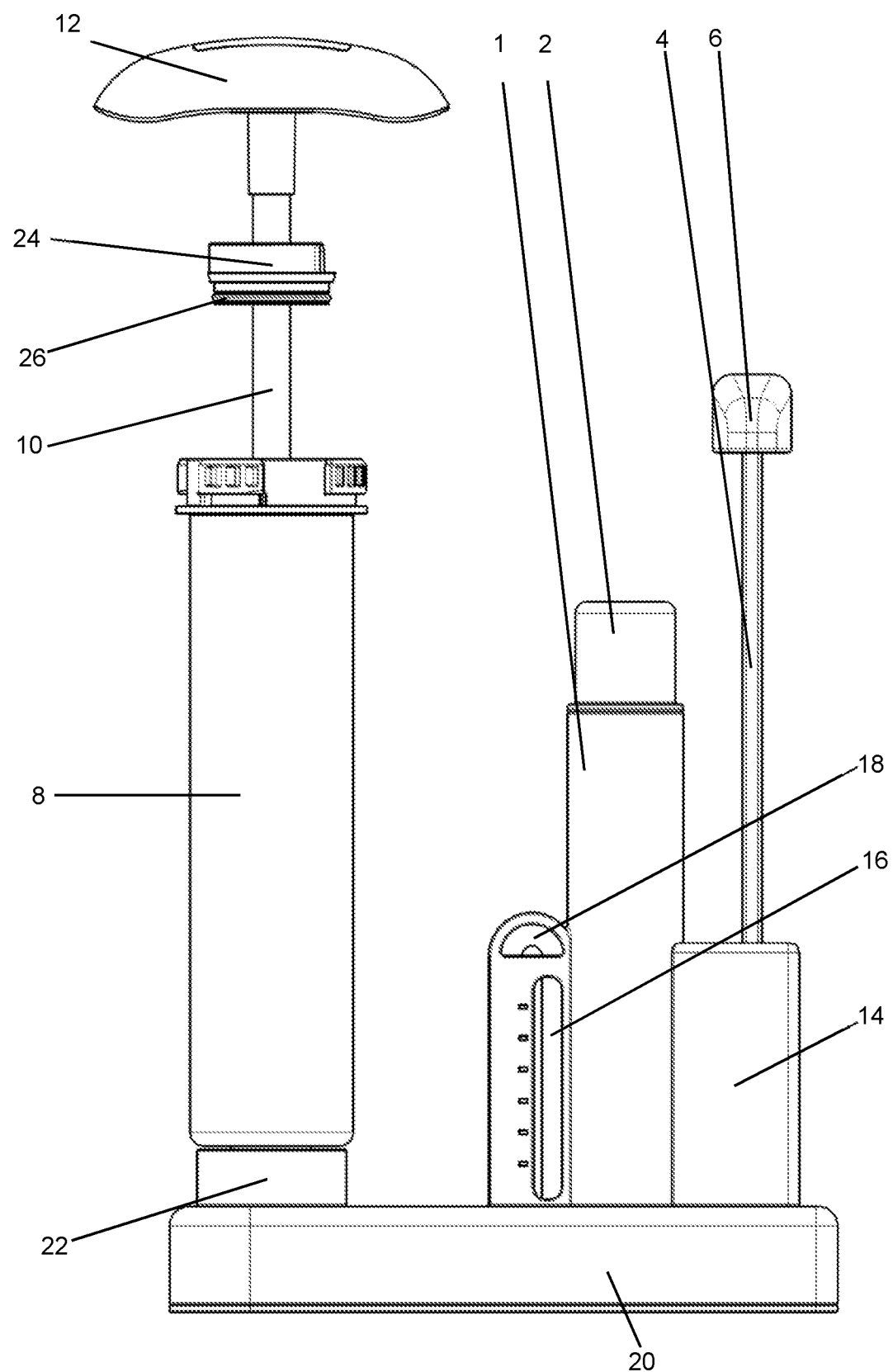

(51) Int. Cl.
  *B01F 13/00* (2006.01)
  *B01F 15/00* (2006.01)
  *B67B 7/92* (2006.01)
  *A61B 17/88* (2006.01)

(52) U.S. Cl.
  CPC ........ *B01F 3/1271* (2013.01); *B01F 13/0023* (2013.01); *B01F 15/00974* (2013.01); *B01F 15/0243* (2013.01); *B01F 15/0278* (2013.01); *B67B 7/92* (2013.01); *A61B 2017/8838* (2013.01); *B01F 2215/0029* (2013.01)

(58) Field of Classification Search
  CPC . B65D 83/687; A61M 5/2425; A61M 35/003; A61M 35/006; A61J 1/065
  USPC ........................................................ 206/532
  See application file for complete search history.

(56) References Cited

U.S. PATENT DOCUMENTS

| | | | |
|---|---|---|---|
| 5,588,745 | A | 12/1996 | Tanaka et al. |
| 5,997,544 | A | 12/1999 | Nies et al. |
| 6,709,149 | B1 | 3/2004 | Tepic |
| 7,073,936 | B1 | 7/2006 | Jonsson |
| 7,516,872 | B2 * | 4/2009 | Boone .............. A61B 17/00491 206/532 |
| 7,909,808 | B2 | 3/2011 | Stenton |
| 8,323,260 | B2 | 12/2012 | Stenton |
| 2006/0049203 | A1 | 3/2006 | Boone et al. |
| 2010/0329074 | A1 | 12/2010 | Vogt et al. |
| 2011/0114212 | A1 | 5/2011 | Greter et al. |
| 2011/0137339 | A1 | 6/2011 | Stenton |
| 2012/0006874 | A1 | 1/2012 | Vogt et al. |
| 2012/0160867 | A1 | 6/2012 | Goodman et al. |
| 2013/0135959 | A1 | 5/2013 | Vogt et al. |

FOREIGN PATENT DOCUMENTS

| | | | |
|---|---|---|---|
| DE | 694 05 579 | T2 | 2/1998 |
| DE | 19841722 | A1 | 3/2000 |
| DE | 69812726 | T2 | 2/2004 |
| DE | 602004011934 | T2 | 2/2009 |
| DE | 102009031178 | B3 | 9/2010 |
| DE | 102010026496 | A1 | 1/2012 |
| EP | 0079983 | A1 | 6/1983 |
| EP | 0692229 | A1 | 1/1996 |
| EP | 0972499 | A2 | 1/2000 |
| WO | 2010012114 | A1 | 2/2010 |
| WO | 2011/003625 | A1 | 1/2011 |
| WO | WO-2011003625 | A1 * | 1/2011 ......... A61B 17/8833 |

OTHER PUBLICATIONS

European Search Report for corresponding European Application No. 16189604.8, dated Mar. 14, 2017.

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.

* cited by examiner

DEVICE AND METHOD FOR MANUALLY OPENING GLASS AMPULES AND A CEMENTING DEVICE

This application claims foreign priority benefit under 35 U.S.C. 119 of German Application No. DE 10 2015 116 245.8 filed Sep. 25, 2015.

The invention relates to a device for manually opening glass ampules within the device and to a medical cementing device with such a device. Further, the invention relates to a method for opening glass ampules in such a device.

The subject of the invention are thus a device for opening glass ampules, a method for opening glass ampules and medical cementing devices, in particular full-pre-packed mixing systems, with the device for opening glass ampules for storing and mixing components of PMMA bone cement.

Small volumes of volatile organic fluids, such as methyl methacrylate, can be stored in plastic bags, plastic containers and glass ampules. Glass ampules have the decisive advantage over packaging means made of plastic or plastic multi-layer systems in that they are entirely impermeable. No migration of fluids occurs through the glass wall. With packaging means made of plastic and plastic multi-layer systems, low-level losses are always observed as a result of the migration of the organic fluid through the plastic layers. Further, the low-cost manufacture and filling of glass ampules is possible on an industrial scale.

For polymethyl methacrylate bone cements (PMMA bone cements) which are constructed from a fluid monomer component and a powder component, the monomer fluid is usually stored in glass ampules (Kühn, K.-D.: Knochenzemente für die Endoprothetik, Springer Verlag Berlin Heidelberg New York, 2001). Glass ampules can be opened by breaking the glass wall at a specified set breakpoint. However, with direct manual opening of the glass ampules, there is a risk that the user will suffer injury from cuts.

An advantageous development in cementing technology are cementing devices in which both the cement powder and the monomer fluid are already packaged in separate compartments of the mixing system and are only mixed with each other directly prior to the cementing application in the cementing device. Such full-pre-packed cementing devices have been recommended by EP 0 692 229 A1, DE 10 2009 031 178 B3, U.S. Pat. Nos. 5,997,544 A, 6,709,149 B1, DE 698 12 726 T2 and U.S. Pat. No. 5,588,745 A.

A series of devices is described with which glass ampules can be opened within the devices. With these devices, the risk of injury from cuts by the user is securely prevented. Further, the user is protected by the devices against direct contact with the fluids during opening and emptying the glass ampules when storing fluids in the glass ampules which are hazardous to health.

Devices for opening glass ampules can be divided into two groups. With the first group, the head of the ampule is separated from the ampule body through shearing. With the second group, the ampule body or ampule floor itself is broken.

A closed device is known from DE 198 41 722 A1 with which the ampule head is supported on a rotatable shaft, and the ampule body is affixed in a closed container. When the shaft is turned from the outside, the ampule head is separated from the ampule body through shearing.

A similar device is disclosed in DE 29 21 565 A1. Here, a hollow lever is placed onto an ampule head, wherein the ampule is affixed in a container. The lever can be moved from the outside, as a result of which the ampule head is broken off from the ampule body.

In EP 0 079 983 A1, a cementing device is proposed with which the ampule head is supported in a rigid roll-shaped body which is attached to a cartridge, wherein an ampule holder which retains the ampule body is pivoted around the longitudinal axis of the roll-shaped body. When the ampule holder is turned around the rotational axis of the rigid roll-shaped body, the ampule body breaks off from the ampule head which does not turn with it and the fluid can then be suctioned into the adjacent cartridge by means of a vacuum effect.

A device which functions according to the same principle is proposed with WO 2010/012 114 A1. There, the ampule head is arranged in a roll body which is to be manually rotated from the outside, wherein the roll body is arranged in a cylindrical opening of a rigid ampule holder. When the roll body is manually rotated, the ampule head which is also turned during the rotational movement of the roll body breaks away from the affixed ampule body and the ampule is thus opened. The disadvantage of this device is the relatively complex sealing of the roll body in the cylindrical opening of the ampule holder. Fluids can only run independently out of the broken ampule when the ampule has an angle of approximately 45° to the vertical or when with the ampule body in a vertical bearing, the profile of the neck of the ampule is so large that the surface tension of the fluid is overcompensated by gravity.

In DE 10 2010 026 496 A1 a simple, robust device for opening glass ampules is described. With this device, the ampule body is arranged in an elastically deformable ampule holder, which is connected to a rigid hollow body for retaining an ampule head. Here, the ampule head lies in a rigid hollow cylinder the diameter of which is larger than or equal to the length of the ampule head. When the ampule holder is moved counter to the longitudinal axis of the ampule holder, the ampule body is broken away from the ampule head. The ampule head falls downwards and can turn to the side in the hollow cylinder, and remains lying on a fluid-permeable porous disc, through which the fluid can flow out of the ampule.

In EP 0 972 499 A2, it is described that an ampule is supported in a dual-section ampule holder. Both parts of the ampule holder contain threads and can be bolted together using these threads. When bolting the two parts of the ampule holder, the ampule arranged in the ampule holder is pressed with its ampule floor against a tapered cone. As a result, the ampule floor breaks and the fluid can run out of the ampule.

The object of the invention is to overcome the disadvantages of the prior art. In particular, a device that is simple to handle should be provided for opening glass ampules which is as space-saving as possible and which permits a secure opening of the glass ampules, so that the entire fluid runs out of the ampules, regardless of its surface tension. A further object is to provide a method for opening glass ampules. The device to be developed for opening glass ampules should be integrated into full-pre-packed cementing devices for powder-fluid polymethyl methacrylate bone cements. The device should be inexpensive to produce and enable error-free application. Furthermore, the device should be operable without an energy storage device. For medical applications, the device should be designed as a disposable product, so that as far as possible, no metals should be used and it should be aimed to produce a structure made from plastic as far as possible. As a medical mixing system, the device should also enable storage and mixing of a monomer fluid in an ampule with a bone cement powder in a cartridge.

Further, a low-cost and reliably functioning cementing device for mixing a medical cement and if appropriate, for storing the initial components, and a method for opening the glass ampule and for mixing the bone cement should be found, in which manual operation which is as simple as possible can be used.

The main component of the polymethyl methacrylate bone cement as a mix should be a powder, and the second component should be provided in the form of a fluid in the glass ampule. It should preferably be possible to store the two initial components of the bone cement separately in the vacuum mixing system and to securely combine them through the application of the device.

The objects of the invention are attained by means of a device for the manually opening of glass ampules within the device, wherein the device comprises the following parts:
A) a holder with side walls closed at least in sections for holding the glass ampule, wherein the holder comprises at least one deformable closed side wall and opposite the deformable side wall a supporting element is provided,
B) a strainer and/or a filter which is or are arranged below the holder so that the content of the opened glass ampule flows through the strainer and/or the filter,
C) a first lever which is pivotable around a first axis in such a manner that it rotates against the holder, wherein a free end of the first lever is pressed against the deformable side wall of the holder,
D) a second lever which is pivotable around a second axis in such a manner that it rotates against the holder, wherein the second axis divides the second lever into a short lever arm and a long lever arm, wherein one end of the short lever arm is pressable through manual operation of the long lever arm against the first lever in such a manner that the free end of the first lever presses against the deformable side wall and deforms said wall in such a manner that a glass ampule which is located in the holder and which matches the holder is broken open by the pressure of the free end of the first lever.

A glass ampule can be regarded as matching the holder in the sense of the invention when the side walls of the glass ampule are in contact with at least two opposite sides on the holder when the glass ampule is inserted into the holder. Preferably, the walls of a glass ampule inserted into the holder are in contact with the side walls of the holder.

The directions "above" and "below" relate to the set-up of the device or to the direction of flow of the fluid from the glass ampule within the device after said ampule has been opened. The fluid from the opened glass ampule thus flows downwards out of the glass ampule through the strainer and/or filter.

It can be provided according to the invention that the deformable side wall is elastically and/or plastically deformable. The deformable side wall should however be non-destructively deformable within the scope of the deformation provided for the purpose of opening.

It can be provided that a funnel is located below the holder designed to hold and pass on a fluid from the opened glass ampule.

Preferably, the glass ampules have a cylindrical ampule body.

The supporting element must merely be sufficient to hold the glass ampule in position until the glass ampule breaks open due to a force effect through the deformable side wall.

With the device according to the invention it can be provided that the holder is a hollow cylinder and/or the holder consists of an elastomer or an insertion made of an elastomer, wherein preferably, the elastomer has a Shore hardness of greater than 60, wherein in a particularly preferred manner, the elastomer is a silicon rubber or an ethylene propylene diene rubber (EPDM).

Due to the cylindrical geometry of the holder, it is achieved that a cylindrical glass ampule can be inserted into the holder with a firm seat. With the given Shore hardness, it is achieved that the glass ampule can be securely opened within the holder without the holder being destroyed or a leakage developing.

According to a preferred further embodiment of the present invention, it can be provided that a ledge for placing on the glass ampule is arranged in the holder, wherein the ledge is smaller than half the area of the surface of the ampule floor or the ampule profile.

As a result, the glass ampule is affixed in the holder so that it is to be broken open in a defined position with the aid of the lever and cannot be displaced. The ledge is preferably arranged in the holder in such a manner that the distance between the ledge and the fluid-permeable strainer and/or filter is the same as or greater than the diameter of the glass ampule.

With embodiments with a ledge it can be provided that the ledge is arranged in the holder in such a manner that the distance between the ledge and the strainer and/or filter is the same as or greater than the outer diameter of the glass ampule to be used.

It can hereby be ensured that the ampule floor can fully be held between the ledge and the strainer and/or filter without blocking the fluid flow from the opened glass ampule.

Further, with embodiments with a ledge, it can be provided that the ledge is arranged in the holder in such a manner that the glass ampule stands on the ledge in such a manner that the free end of the first lever lies above the ampule floor on the outer side of the deformable side wall.

As a result, the force of the first lever acts in the area of the ampule floor and thus the ampule floor can be broken off.

Further, it is recommended with the present invention that when the second lever is operated, the free end of the first lever presses onto the deformable side wall in such a manner that the vector of the force comprises a component which is oriented in the direction of the strainer and/or filter and/or which presses the glass ampule, which i9s placed in the holder, into the holder, preferably in the direction of the ledge.

As a result, it is achieved that the glass ampule cannot be pressed out of the holder when the lever is operated, and the positioning of the glass ampule is secured. Consequently, the glass ampule is securely broken open and cannot be displaced by moving out of the holder.

In a preferred embodiment, it can be provided that on the free end of the first lever on the side facing towards the holder, a cutting edge is arranged.

With the cutting edge, a defined force is applied to a small area of the glass ampule so that the glass ampule can be broken open with the lowest possible force effort at a point which is as precisely defined as possible. This cutting edge can be triangular or wedge-shaped. It is also possible that the cutting edge is designed as a pyramid, a prism or as a cone.

For improved force transmission, it can be provided according to the invention that the length ratio between the long lever arm and the short lever arm is at least 5 to 1.

As a result, a force transfer is achieved so that manual opening of the glass ampule is manually possible in the device which a high degree of force being required.

Further, it can be provided that a glass ampule is arranged in the holder, the glass ampule containing a fluid, preferably a monomer liquid for producing a medical bone cement.

As a result, the device can be used directly to open the glass ampule without having to first insert the glass ampule.

According to a preferred further development of the present invention, it can be provided that the second lever is rotatable in the same plane as the first lever, wherein the movement of the second lever engages with the movement of the first lever.

As a result, it is ensured that the first lever either moves with or an be operated with the second lever.

Further, it can be provided that the second axis of the second lever is arranged above the first axis of the first lever, wherein preferably, the first axis of the first lever and the second axis of the second lever are arranged parallel to each other.

As a result, it is achieved that the first lever can be operated from above with the second lever. In a particularly preferred manner, it can be provided that the long lever arm is arranged above the second axis of the second lever, and the short lever arm is arranged below the second axis. The free end of the first lever is additionally arranged above the first axis. Further, it can be provided that the short lever arm of the second lever is in contact with the free end of the first lever. Further, it can be provided that the short lever arm of the second lever is arranged between the second axis of the second lever and the free end or the first axis of the first lever. With all these measures, the operability of the device is improved.

The objects that form the basis of the present invention are also attained by means of a medical cementing device, in particular a full-pre-packed medical cementing device for mixing a PMMA bone cement, comprising such a device for manually opening glass ampules within the device according to the invention, further comprising a cartridge with a mixing chamber containing a cement powder, in particular a bone cement powder, wherein the mixing chamber is connected with the holder below the strainer or the filter in such a manner that it is permeable to liquids.

The device can be particularly advantageously used in connection with medical cementing devices.

Here, it can be provided that a glass ampule is arranged in the holder, the glass ampule containing a monomer liquid, a pump, with which the monomer liquid is to be pumped into the cartridge, a connection line, through which the monomer liquid is to be transported from the glass ampule into the cartridge, a manually operated stirring unit, with which the content of the cartridge can be mixed, a delivery piston which is provided in the cartridge in such a manner that it can be moved in the longitudinal direction and by which the mixed bone cement is to be discharged from the cartridge, a gas-permeable connection means in the delivery piston, which connects the inner chamber of the cartridge with the external environment and a foot element which is connected to the holder, the cartridge and the levers, and with which the cementing device can be placed onto an even surface.

The pump can be driven manually or with a pre-tensioned spring.

In this manner, a finished medical cementing device is provided which uses the device for opening the glass ampule.

With the invention, it is also recommended that the delivery piston closes the mixing chamber of the cartridge in a gas-tight manner with the exception of the gas-permeable connection.

With such cementing devices, it can also be provided that the pump is a suction pressure pump, wherein the pressure pump element of the suction pressure pump is connected to the holder and the suction pump element of the suction pressure pump is connected to the mixing chamber of the cartridge, preferably connected to the mixing chamber of the cartridge via the gas-permeable connection means in the delivery piston.

The objects that form the basis of the invention are further attained by a method for opening a glass ampule in such a device or cementing device, in which the long lever arm of the second lever is manually rotated around the second axis, as a result of which the short lever arm of the second lever is pressed onto the free end of the first lever, so that the first lever rotates around the first axis and the free end of the first lever presses onto the deformable side wall of the holder, the deformable side wall deforms and through the deformation of the deformable side wall a glass ampule in the holder is mechanically broken open.

Here it can be provided that the glass ampule is inserted into the holder prior to the manual operation of the second lever, preferably with the ampule floor of the glass ampule inserted first into the holder.

Further it can be provided that following the breaking open of the glass ampule, a monomer liquid runs out of the glass ampule through the strainer and/or the filter and is transported into a mixing chamber of the cartridge in which a bone cement powder is located, wherein subsequently, the bone cement powder and the monomer liquid are mixed in the mixing chamber of the cartridge.

The invention is based on the surprising finding that with the device according to the invention, it is possible to break open a glass ampule over a large area within the device or the cementing device so that the monomer fluid flows out of the glass ampule within a short space of time and is available for mixing with a medical bone cement powder. With the aid of the two levers which are actively connected to each other, it is possible to direct the pressure onto the glass ampule in the direction of the seat of the glass ampule in the holder, so that a displacement of the glass ampule out of the holder can be precluded. At the same time, a very precisely defined local pressure can be applied to the glass ampule, with which the glass ampule can be broken open in the device. With the aid of the deformable side wall, it can be provided that the force is transferred through this side wall into the interior of the holder onto the glass ampule, wherein the holder remains closed during this procedure. An exit of the fluid out of the holder can thus be precluded. With the aid of the strainer and/or the filter, glass splinters which can be created when the glass ampule is opened can be withheld. The monomer fluid is then suitable for use for mixing with the bone cement powder.

The particular advantage of the device according to the invention is that any ampules required, regardless of the ampule length and the geometry of the ampule head, can be securely opened when the ampule diameter is the same or somewhat larger than the inner diameter of the ampule holder or of the holder. Further it is a particular advantage that when the ampule wall is broken, the fluid contained in the ampule immediately flows out in full, independently of the surface tension. By contrast, with conventional ampule breakers, the fluid flows out considerably more slowly after the ampule head is separated due to the relatively narrow profile of the ampule neck. Here, reasonably fast discharge speeds are only achieved when either the ampule is held at an angle of approx. 45° with the ampule neck pointing downwards, or when the profile of the ampule neck is so large that the surface tension of the fluid cannot hold the meniscus of the fluid in the ampule neck.

An exemplary device for opening glass ampules according to the invention can for example be composed of a) a hollow cylinder as a holder with at least one deformable surface for holding at least one glass ampule
b) a non-deformable supporting element opposite the deformable sheath surface of the hollow cylinder
c) a fluid-permeable strainer plate which is arranged below the hollow cylinder
d) a funnel which is arranged below the strainer plate
e) a first lever which is adjoined in such a manner that it can be pivoted onto a first joint in such a manner that the free end of the lever is in contact on the elastically deformable outer surface of the hollow cylinder
f) a second lever which is divided by a second joint into a short lever section and a long lever section, wherein the centre of rotation of the second lever is arranged equal to or higher than the centre of rotation of the first lever
g) the second lever is arranged parallel to the hollow cylinder, wherein the short lever section is arranged parallel to the first lever, and
h) wherein when the long lever section of the second lever is turned around the second centre of rotation contrary to the hollow cylinder, the short lever section is pressed against the free end of the first lever, wherein the first lever is turned around the second centre of rotation and is pressed against the deformable sheath surface of the hollow cylinder while deforming the sheath surface, and the at least one ampule is broken in the hollow cylinder against the non-deformable supporting element.

A method for opening ampules according to the invention with the device described as an example can for example be characterized by the following chronological steps:
a) the long lever section of the second lever is manually turned around the second centre of rotation contract to the holder, which is formed as a hollow cylinder,
b) the short lever section presses onto the free end of the first lever during its rotational movement around the second centre of rotation
c) the free end of the first lever is pressed onto the deformable outer surface of the hollow cylinder
d) the deformed surface of the hollow cylinder is pressed onto the sheath surface of the ampule, wherein the ampule is pressed against the non-deformable supporting element and breaks apart, wherein the glass splinters fall onto the fluid-permeable strainer element, and
e) the fluid flows out of the broken ampule through the strainer element into the funnel.

Further, a full-pre-packed cementing device with the device for opening glass ampules is provided according to the invention. The full-pre-packed cementing device is composed of the following:
a) a hollow cylinder as a holder with at least one deformable surface for holding at least one glass ampule,
b) at least one glass ampule which contains the monomer fluid and which is arranged in the hollow cylinder,
c) a non-deformable supporting element opposite the deformable sheath surface of the hollow cylinder,
d) a fluid-permeable strainer plate which is arranged below the hollow cylinder,
e) a funnel which is arranged below the strainer plate,
f) a first lever which is adjoined such that it can be pivoted onto a first joint in such a manner that the free end of the first lever lies in contact on the elastically deformable outer surface of the hollow cylinder,
g) a second lever which is divided by a second joint into a short lever section and a long lever section, wherein the centre of rotation of the second lever is arranged equal to or higher than the centre of rotation of the first lever,
h) the second lever is arranged parallel to the hollow cylinder, wherein the short lever section is arranged parallel to the first lever,
i) a cartridge in the form of a hollow cylinder,
j) cement powder which is arranged in the inner chamber of the cartridge,
k) a fluid-permeable connection means which connects the funnel to the hollow chamber of the cartridge,
l) a manually operated stirring unit, wherein the stirring element is arranged in the cartridge,
m) a piston which can be axially displaced in the cartridge, which closes the inner chamber of the cartridge in a gas-tight manner,
n) a gas-permeable connection means in the piston which connects the inner chamber of the cartridge with the outer atmosphere in a gas-permeable manner, and
o) as an option, a foot element which is connected to the hollow cylinder, the cartridge, the first lever and the second lever.

A second alternative full-pre-packed cementing device with the device for opening glass ampules can for example be composed of the following:
a) a hollow cylinder with at least one deformable surface for holding at least one glass ampule
b) at least one glass ampule which contains the monomer fluid and which is arranged in the hollow cylinder,
c) a non-deformable supporting element opposite the deformable sheath surface of the hollow cylinder,
d) a fluid-permeable strainer plate which is arranged below the hollow cylinder,
e) a funnel which is arranged below the strainer plate,
f) a first lever which is adjoined such that it can be pivoted onto a first joint in such a manner that the free end of the first lever lies in contact on the elastically deformable outer surface of the hollow cylinder,
g) a second lever which is divided by a second joint into a short lever section and a long lever section, wherein the centre of rotation of the second lever is arranged higher than the centre of rotation of the first lever,
h) the second lever is arranged parallel to the hollow cylinder, wherein the short lever section is arranged parallel to the first lever,
i) a cartridge in the form of a hollow cylinder,
j) cement powder which is arranged in the inner chamber of the cartridge,
k) a fluid-permeable first connection means which connects the funnel to a piston pump which is manually driven or driven by a spring force,
l) a fluid-permeable second connection means which connects the piston pump with the inner chamber of the cartridge in a fluid-permeable manner
m) a manually operated stirring unit, wherein the stirring unit is arranged in the cartridge,
n) a piston which is axially displaceable in the cartridge, which closes the inner chamber of the cartridge in a gas-tight manner,
o) a gas permeable second connection means in the piston which connects the inner chamber of the cartridge with the outer atmosphere, and
p) as an option, a foot element which is connected to the hollow cylinder, the cartridge, the first lever and the second lever.

A third full-pre-packed cementing device with the device for opening glass ampules is for example composed of the following:
a) a hollow cylinder with at least one deformable surface for holding at least one glass ampule b) at least one glass ampule which contains the monomer fluid and which is arranged in the hollow cylinder
c) a non-deformable supporting element opposite the deformable sheath surface of the hollow cylinder
d) a fluid-permeable strainer plate which is arranged below the hollow cylinder
e) a funnel which is arranged below the strainer plate
f) a first lever which is adjoined such that it can be pivoted onto a first joint in such a manner that the free end of the first lever lies in contact on the elastically deformable outer surface of the hollow cylinder
g) a second lever which is divided by a second joint into a short lever section and a long lever section, wherein the centre of rotation of the second lever is arranged higher than the centre of rotation of the first lever
h) the second lever is arranged parallel to the hollow cylinder, wherein the short lever section is arranged parallel to the first lever
i) a cartridge in the form of a hollow cylinder
j) cement powder which is arranged in the inner chamber of the cartridge
k) a fluid-permeable first connection means which connects the funnel with the inner chamber of the cartridge in a fluid-permeable manner
l) a manually operated stirring unit, wherein the stirring unit is arranged in the cartridge
m) a piston which is axially displaceable in the cartridge, which closes the inner chamber of the cartridge in a gas-tight manner
n) a gas permeable second connection means in the piston which connects the inner chamber of the cartridge with the outer atmosphere
o) a vacuum pump which is manually driven or driven by a spring force, which is connected by a third connection means to the gas permeable second connection means in the piston, and
p) as an option, a foot element which is connected to the hollow cylinder, the cartridge, the first lever and the second lever.

A fourth full-pre-packed cementing device with the device for opening glass ampules is for example composed of the following:
a) a suction pressure pump which when actuated synchronously suctions and pumps, and which is manually driven or driven by a spring force
b) a hollow cylinder with at least one deformable surface for holding at least one glass ampule
c) at least one glass ampule which contains the monomer fluid and which is arranged in the hollow cylinder
d) a non-deformable supporting element opposite the deformable sheath surface of the hollow cylinder
e) a fluid-permeable strainer plate which is arranged below the hollow cylinder
f) a funnel which is arranged below the strainer plate
g) a first lever which is adjoined such that it can be pivoted onto a first joint in such a manner that the free end of the first lever lies in contact on the elastically deformable outer surface of the hollow cylinder
h) a second lever which is divided by a second joint into a short lever section and a long lever section, wherein the centre of rotation of the second lever is arranged higher than the centre of rotation of the first lever
i) the second lever is arranged parallel to the hollow cylinder, wherein the short lever section is arranged parallel to the first lever
j) a cartridge in the form of a hollow cylinder
k) cement powder which is arranged in the inner chamber of the cartridge
l) a fluid-permeable first connection means which connects the funnel with a pressure pump part of the double-acting pump
m) a fluid-permeable second connection means which connects the pressure pump part of the suction pressure pump with the inner chamber of the cartridge
n) a manually operated stirring unit, wherein the stirring unit is arranged in the cartridge
o) a piston which is axially displaceable in the cartridge, which closes the inner chamber of the cartridge in a gas-tight manner
p) a gas permeable third connection means in the piston which connects the inner chamber of the cartridge with the outer atmosphere
q) a gas permeable fourth connection means which connects the suction pump part of the suction pressure pump with the gas permeable third connection means in the piston, and
r) as an option, a foot element which is connected to the hollow cylinder, the cartridge, the first lever and the second lever.

Figure 2:
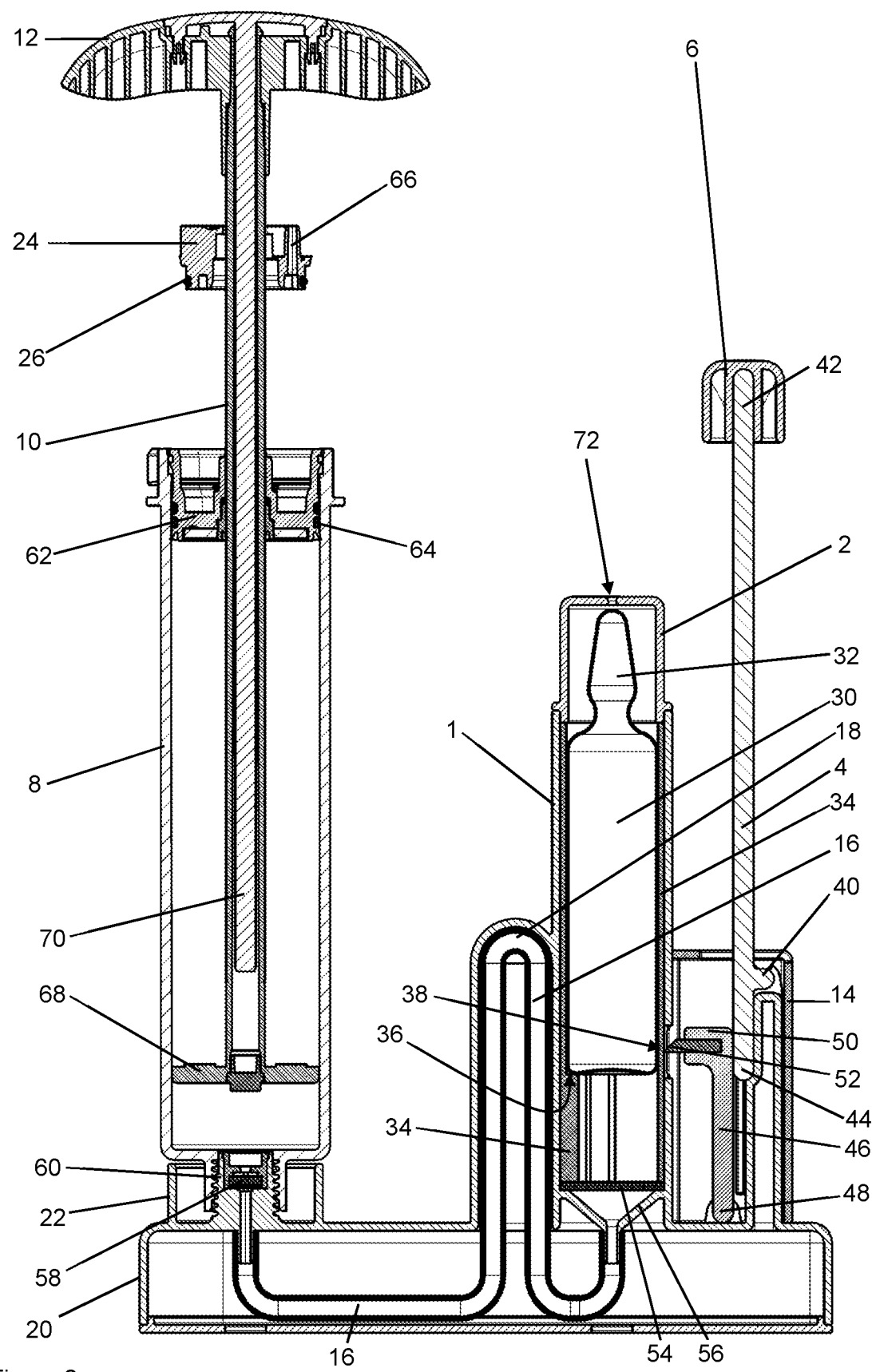
Figure 3:
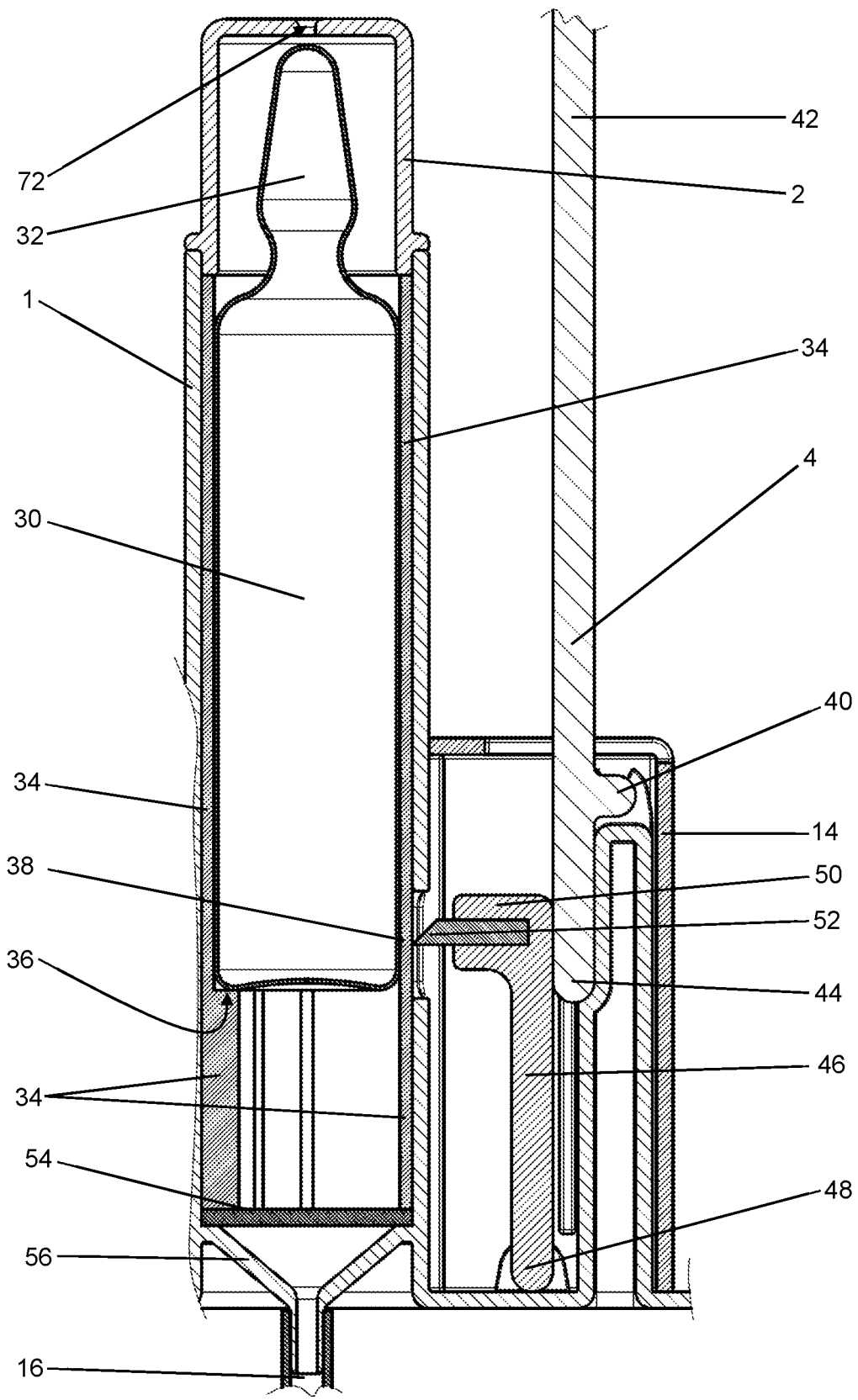
Figure 4:
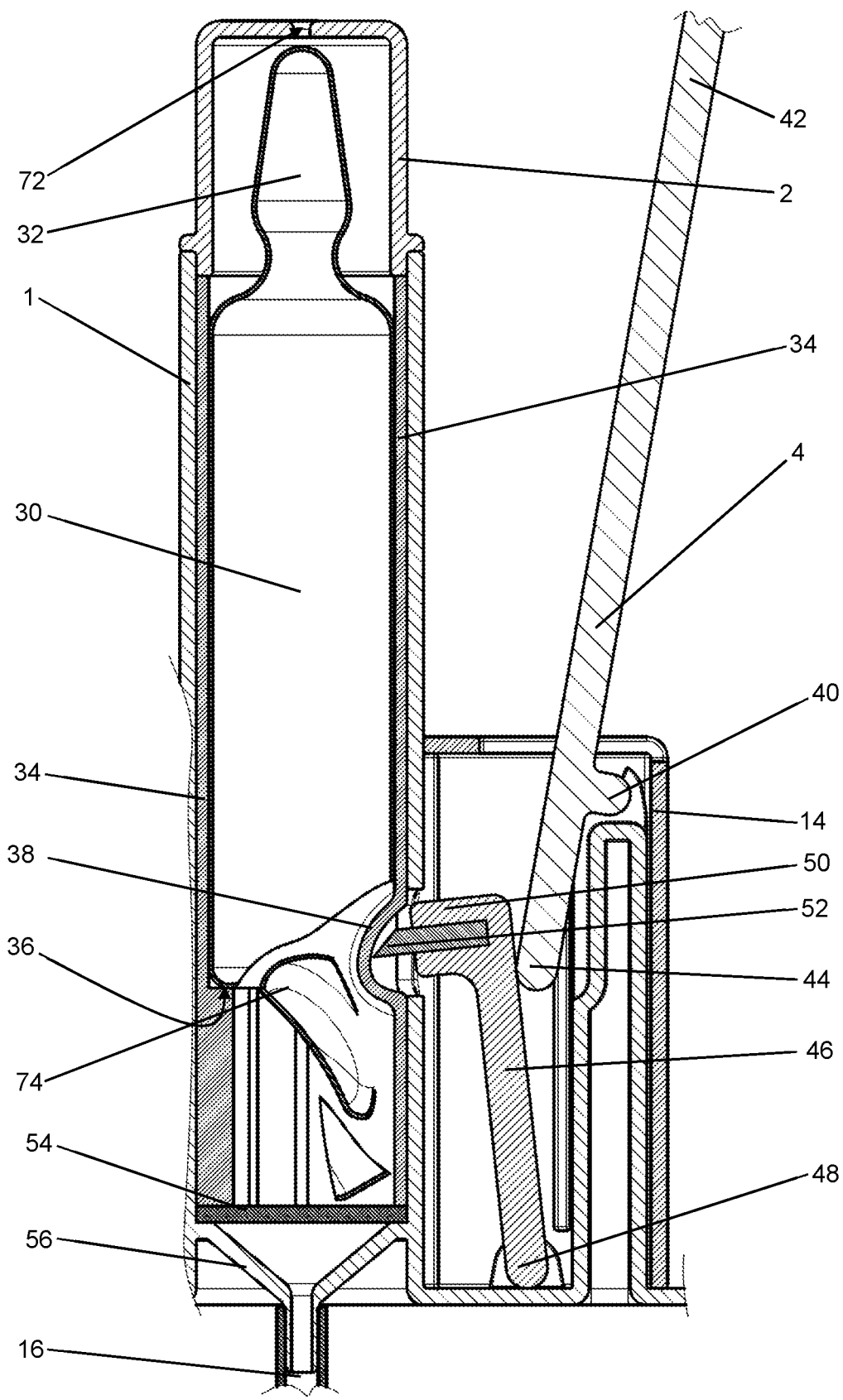
Figure 5:
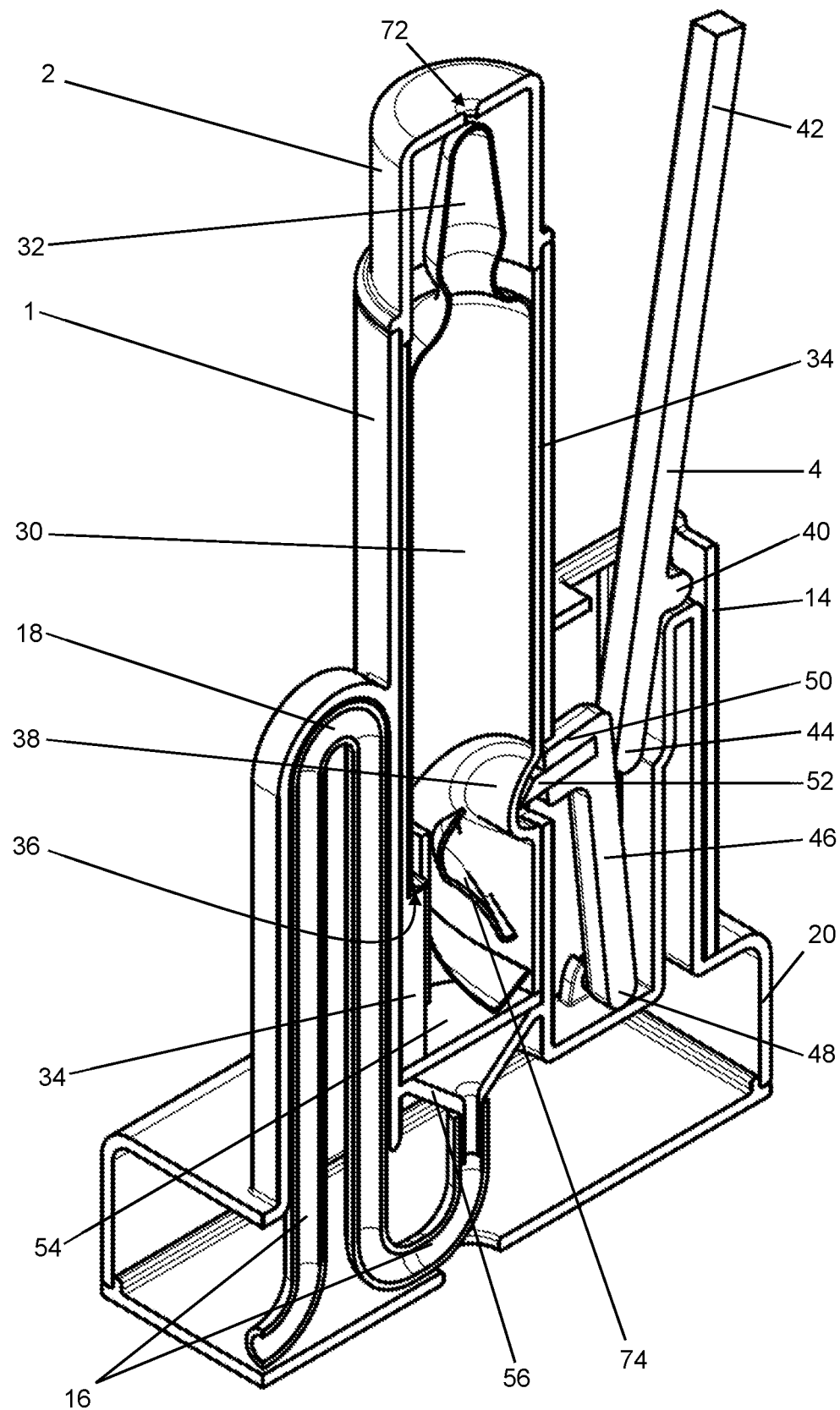

Below, further exemplary embodiments of the invention will be explained with reference to five schematic drawings, although without at the same time restricting the invention, in which:

FIG. 1: shows a schematic side view of a cementing device according to the invention with a device according to the invention for opening glass ampules;

FIG. 2: shows a schematic profile view of the cementing device according to FIG. 1;

FIG. 3: shows a schematic detail profile view of the device according to the invention for opening glass ampules as a part of the cementing device as shown in FIGS. 1 and 2 before breaking open the glass ampule;

FIG. 4: shows a schematic detail profile view of the device according to the invention for opening glass ampules as shown in FIG. 3 after the glass ampule has been broken open; and FIG. 5: shows a schematic perspective profile view of a part of the cementing device as shown in FIGS. 1 and 2.

FIGS. 1 to 5 show different views of a cementing device according to the invention and a device for opening glass ampules according to the invention as part of said cementing device. FIG. 1 shows a schematic side view of a cementing device according to the invention with a device for opening glass ampules according to the invention. The cementing device comprises an ampule holder 1, which is closed on the upper side (in FIG. 1 above) with a lid 2. In the interior of the ampule holder 1, a glass ampule (not shown in FIG. 1) is contained which can be opened within the ampule holder 1 or within the device for opening the glass ampule. The lid 2 can simply be inserted into the ampule holder 1 in order to close the inner chamber of the ampule holder 1. Next to the ampule holder 1, a lever 4 is provided which ends in a grip 6. The lever 4 can be manually turned or tipped against the ampule holder 1 with the aid of the grip 6 in the direction away from the ampule holder 1 and the lid 2 in order to operate the cementing device or the device for opening the glass ampule.

Furthermore, a cartridge 8 is arranged next to the ampule holder 1, in which a bone cement powder is arranged. A mixing tube 10 which ends in a grip 12 protrudes into a mixing chamber of the cartridge 8, which is formed by the inner chamber of the cartridge 8. The mixing tube 10 is additionally supported in such a manner that it is rotatable and displaceable in the longitudinal direction, in a passage which leads into the interior of the cartridge 8.

The lever 4 is supported in such a manner that it can be turned against the ampule holder 1 within a housing 14. The housing 14, the grips 6, 12, the mixing rod 10, the cartridge 8, the lever 4, the lid 2 and the ampule holder 1 are made of plastic and can be produced using a simple injection moulding method. The ampule holder 1 ends in a connection line 16, which connects the ampule holder 1 with the mixing chamber of the cartridge 8 in a fluid-permeable manner. The connection line 16 forms a loop 18 or a siphon 18 to prevent a fluid from flowing out of the opened glass ampule in the ampule holder 1 and into the mixing chamber of the cartridge 8 directly after the glass ampule has been opened. The connection line 16 is transparent and can be observed by the user through a window in the housing in the area of the loop 18. As a result, the user has the opportunity of visually checking whether the fluid is being guided into the mixing chamber of the cartridge 8. Additionally, a scale can be provided in the area of the window with which the user can check the quantity of the fluid that has been introduced or is present in the ampule holder 1.

The ampule holder 1, the housing 14 and the cartridge 8 are supported by a foot element 20 made of plastic. The foot element 20 can be designed as a single piece with the ampule holder 1 and the housing 14. The foot element 20 has an even underside, so that the cementing device can be set conveniently on an even base, such as a table. In the foot element 20, a connecting piece 22 is arranged for clamping and affixing the cartridge 8.

A sealing piston 24 as part of a two-part delivery piston is arranged around the mixing tube 10. The mixing tube 10 extends in the longitudinal direction through a passage in the sealing piston 24 in such a manner that it can be pivoted and displaced. A circumferential seal 26 made of rubber is arranged on the sealing piston 24, with which the sealing piston 24 can be sealed against a sterilization piston (not shown in FIG. 1, but shown in FIGS. 2 to 5) as a second part of the delivery piston when the sealing piston 24 is inserted into the sterilization piston. The sterilization piston is already inserted above in the cartridge 8 and closes the mixing chamber of the cartridge 8 against the environment in a gas-permeable manner, while being impermeable for the bone cement powder. The sealing piston 24 and the sterilisation piston can be produced from plastic with the exception of the seal 26 and the seals of the sterilization piston.

FIG. 2 shows a schematic profile view of the cementing device as shown in FIG. 1. Here, it can be seen that in the interior of the ampule holder 1, a glass ampule 30 is located. The glass ampule 30 is filled with a monomer fluid. FIG. 3 shows a schematic detail profile view of the device according to the invention for opening glass ampules as part of the cementing device as shown in FIGS. 1 and 2 prior to breaking open the glass ampule 30. The monomer fluid forms a bone cement mixture with the cement powder from the cartridge 8 when they are mixed together. The glass ampule 30 comprises an ampule head 32 which is usually broken off in order to open the glass ampule 30. Since the glass ampule 30 has a thin neck, this causes the monomer fluid to flow out of the glass ampule 30 only slowly, and thus the user must wait until they can implement the next steps for operating the cementing device.

The glass ampule 30 is inserted in an insert 34 made of a deformable material. The insert 34, together with the ampule holder 1, forms a holder 1, 34 for the glass ampule 30. The insert 34 is designed with several thickened areas in the lower section, which form a ledge 36, on which the ampule floor sits. The ampule floor is located on the side of the glass ampule 30 opposite the ampule head 32. The glass ampule 30 can therefore only be inserted into the insert of the ampule holder 1 up to the ampule floor.

The ampule holder 1 comprises a side opening, in which the insert 34 forms a deformable side wall 38. At this point, the glass ampule 30 can be opened or broken open, whereby a pressure acts through the deformable side wall 38 onto the glass ampule 30 just above the ampule floor. When the ampule floor of the glass ampule 30 is broken off or when the glass ampule 30 is opened, the monomer fluid can flow in the full profile out of the opened glass ampule 30, so that the monomer fluid is quickly available to its full extent for further processing within the cementing device or within the device for opening the glass ampule 30 of the cementing device.

In order to deform the side wall 38 and thus to break open the glass ampule 30, the lever 4 is used, which is operated via the grip 6 and turned around an axis 40. The lever 4 is supported against the housing 14 in such a manner that it can be pivoted or turned around the axis 40. The axis 40 divides the lever 4 into a long lever arm 42 on which the grip 6 is affixed and a short lever arm 44 which is arranged within the housing 14. As presented, the long lever arm 42 can only be moved away from the ampule holder 1 and not towards it, since the short lever arm 44 on the foot element 20 or the housing 14 lies in contact on the side opposite the ampule holder 1 (in FIGS. 2 and 3, right), and thus blocks a rotation in this direction.

The short lever arm 44 of the lever 4 lies on its side facing the ampule holder 1 in contact with a further shorter lever 46, which is connected via a joint 48 or an axis 48 such that it can be pivoted around the axis 48 with the foot element of the cementing device or the device for opening the glass ampule 30. This additional lever 46 is arranged within the housing 14. The free lever end 50 of the lever 46 in the housing 14 can be moved with the short lever arm 44. At the tip of the free lever end 50, a cutting edge 52 is attached which lies in contact on the deformable side wall 38. The axis 48 of the lever 46 is here arranged in such a manner that the free lever end 50 and thus the cutting edge 52 moves in the direction of the deformable side wall 38 and the foot element 20. As a result, it is achieved that the force which can be applied by the cutting edge 52 through the deformable side wall 38 onto the glass ampule 30, also lightly presses the glass ampule 30 in the direction of the ledge 36 and thus presses the glass ampule 30 into the holder 1, 34.

Below the ledge 36, a strainer 54 and/or a filter 54 is arranged with which glass splinters from the opened or broken open glass ampule 30 can be withheld. The distance between the ledge 36 and the strainer 54 and/or filter 54 is greater than the outer diameter of the glass ampule 30, so that the ampule floor which falls off can turn in the interim chamber and does not prevent the outflow of the monomer fluid from the opened glass ampule 30. Below and strainer 54 and/or the filter 54, a funnel 56 is arranged which ends in the connection line 16. Additionally, a valve element (not shown) can also be provided at the entrance of the holder 1, 34 into the connection line 16 which can be opened or closed with the aid of a turning lever.

The connection line 16 guides the monomer fluid over the loop 18 to the cartridge 8. In the mouth of the connection line 16 into the cartridge 8, a powder-impermeable but for monomer fluid-permeable filter 58 is arranged. This filter 58 prevents cement powder from entering into the connection line 16 from the mixing chamber of the cartridge 8, reacting with the monomer fluid there and then hardening in the connection line 16 and as a result blocking the connection line even before the monomer fluid has been guided into the cartridge 8 either completely or in the quantity required. The filter 58 is provided in a connecting piece 60 with an external thread. The cartridge 8, which comprises a matching internal thread, is bolted onto said connecting piece 60.

On the upper end of the cartridge 8, the sterilisation piston 62 is arranged inside the cartridge, and is sealed against the inner walls of the cartridge 8 with two circumferential sealing rings 64 made of rubber. The sterilisation piston 62 is gas-permeable, so that via the sterilisation piston 62, the interior of the cartridge 8, i.e. the mixing chamber, can be sterilised with a sterilising gas such as ethylene oxide. The sterilisation piston 62 provides an upward boundary of the mixing chamber in the interior of the cartridge 8. The sterilisation piston 62 can be moved in the longitudinal direction within the cartridge 8 (shown in FIG. 2 from top to bottom) in order to force out the finished cement mixture from the cartridge 8. In the position shown in FIG. 2, the sterilisation piston 62 is arrested, however, in order to prevent an unwanted movement of the sterilisation piston 62. The sealing piston 24 and the sterilisation piston 62 together form a two-part delivery piston 24, 62 for forcing out the content from the cartridge 8. The sealing piston 24 can be inserted into the sterilisation piston 62 from above in order to seal off the piston system 24, 62 or delivery piston 24, 62. In the sealing piston 24, a passage 66 is located for connecting a vacuum source. With the vacuum source, the mixing chamber in the cartridge 8 can be evacuated and additionally, the monomer fluid can be suctioned out of the ampule holder 1 or the connection line 16 into the cartridge 8.

In the interior of the cartridge 8, i.e. in the mixing chamber, a mixing facility is located with several mixing paddles 68 which are attached to the mixing tube 10. In the mixing tube, a rod 70 is located for stabilisation purposes. With the mixing tube 10, the mixing facility or mixing paddles 68 can be turned in the mixing chamber and moved in the longitudinal direction (shown in FIG. 2 from top to bottom) in order to thoroughly mix the content of the cartridge 8 or the monomer fluid with the cement powder. In order to ensure that the monomer fluid can flow well out of the ampule holder 1, a ventilation passage 72 is provided in the lid 2 through which the air can subsequently flow into the ampule holder 1 when the monomer fluid is guided via the funnel 56 and the connection line 16 into the cartridge 8. In the area of the inner wall of the insert 34, grooves can be provided for this purpose, through which the air can subsequently flow past the glass ampule 30.

FIG. 4 shows a schematic detailed profile view of the device according to the invention for opening glass ampules as shown in FIG. 3 after the glass ampule 30 has been broken open, and FIG. 5 shows a schematic-perspective profile view of a part of the cementing device as shown in FIGS. 1 and 2 with an opened glass ampule 30. The ampule floor 74 is broken off from the glass ampule 30 and thus the glass ampule 30 in the cementing device or device for opening the glass ampule 30 is opened. Additionally, the lever 4 has been manually tipped so that the smaller lever 46 in the interior of the housing 14 with the cutting edge 52 has pressed onto the deformable side wall 38 until the ampule floor 74 has been broken off.

In order to prevent the ampule holder 1 on the side opposite the deformable side wall 38 from being too lightly deformed due to the force effect via the lower lever 46, a supporting element is provided which in the present example is formed by the housing, which surrounds the loop 18 of the connection line 16 and which is designed as a single part with the ampule holder 1. The ampule holder 1 itself can however easily form the supporting element. For this purpose, the ampule holder 1 must merely be sufficiently stable, i.e. comprise e.g. a sufficient wall thickness so that the walls of the ampule holder 1 located opposite the deformable side wall 38 cannot be deformed due to the pressure exerted by the lever 46 and transmitted by the cutting edge 52 and the glass ampule 30.

The monomer fluid from the glass ampule 30 runs out and can be used for mixing with the cement powder in the cartridge 8. After the glass ampule 30 has been broken open, the monomer fluid is available in the ampule holder 1 and can be guided through the connection line 16 into the inner chamber of the cartridge 8, in which a low pressure in the inner chamber of the cartridge 8 is used in order to suction the monomer fluid out of the ampule holder 1 into the inner chamber of the cartridge 8. This low pressure can be generated by a pump (not shown). Alternatively, the monomer fluid can also be pressed into the cartridge 8 with a suitable structure (a pressure pump). In the inner chamber of the cartridge 8, the monomer fluid can then be mixed with the cement powder with the mixing paddles 68 under vacuum conditions or subjected to low pressure, in order to generate the bone cement or bone cement paste.

When the initial components in the inner chamber of the cartridge 8 are mixed with the mixing paddles 68, the mixing tube 10 is pulled out upwards as far as possible from the inner chamber of the cartridge 8 and can then be broken off at a set breakpoint. The sealing piston 24 is turned against the sterilisation piston 62 and thus the gas passage through the sealing piston 24 is closed. The vacuum source is separated from the sealing piston 24. The cartridge 8 is unscrewed from the foot element 20 and a discharge tube (not shown) is screwed into the interior thread of the cartridge 8, through which the mixed bone cement can be applied. The supply piston 24, 62, which is composed of the sterilisation piston 62 and the sealing piston 24, is unlatched and can be driven with an application device (not shown) into the interior of the cartridge 8. As a result, the contents of the cartridge 8, i.e. the mixed bone cement, are pressed out from the opposite opening and through the screwed-on discharge tube.

The components of the cementing device can be made of plastic using an injection moulding method with the exception of the glass ampule 30, the filter 58 and the initial components of the bone cement. The conduits 16, 18 can be made from a different plastic material.

With the cementing device described, the two initial components of the bone cement can be stored and mixed under vacuum conditions at any later point in time required. No internal energy storage device such as a battery or tensioned spring is required for opening the glass ampule 30. The energy required to do so is manually applied.

The features of the invention disclosed in the above description and in the claims, figures and exemplary embodiments can be essential both individually and in any combination required for the realisation of the invention in its different embodiments.

LIST OF REFERENCE NUMERALS

1 Ampule holder
2 Lid
4 Lever
6 Grip
8 Cartridge

10 Mixing tube
12 Grip
14 Housing
16 Connection line
18 Loop/siphon
20 Foot element
22 Connecting piece
24 Sealing piston
26 Seal
30 Glass ampule
32 Ampule head
34 Insert
36 Ledge
38 Deformable side wall
40 Rotational axis/bearing
42 Long lever arm
44 Short lever arm
46 Lever
48 Rotational axis/bearing
50 Free lever end
52 Edge
54 Strainer/filter
56 Funnel
58 Powder impermeable and fluid-permeable filter
60 Connecting piece with external thread
62 Sterilisation piston
64 Seal
66 Passage
68 Mixing paddles
70 Rod
72 Ventilation passage
74 Ampule floor

The invention claimed is:

1. A device for manually opening glass ampules within the device, wherein the device comprises:
    a holder with side walls closed at least in sections for holding glass ampules, wherein the holder comprises at least one deformable closed side wall and a supporting element located opposite to the at least one deformable closed side wall;
    at least one selected from a strainer and a filter arranged below the holder so that content of an opened glass ampule is flowable through the at least one selected from the strainer and/or the filter;
    a first lever pivotable around a first axis such that the first lever rotates against the holder, wherein the first lever has a total length defined between a first end and an opposite second end, wherein the first end comprises the first axis and the second end is a free end of the first lever that is pressable against the deformable closed side wall of the holder; and
    a second lever pivotable around a second axis such that the second lever rotates against the holder, wherein the second axis divides the second lever into a short lever arm and a long lever arm,
    wherein one end of the short lever arm is pressable through manual operation of the long lever arm against the first lever such that the free end of the first lever presses against the deformable closed side wall and deforms said deformable closed side wall such that a glass ampule, when located in the holder, is broken open by the pressure of the free end of the first lever.

2. The device according to claim 1, wherein the holder is a hollow cylinder and/or the holder consists of an elastomer or comprises an insertion made of an elastomer.

3. The device according to claim 1, further comprising:
    a ledge for placing on a glass ampule arranged in the holder, wherein the ledge is smaller than half the area of the surface of the ampule floor or the ampule profile of a glass ampule to be held by the holder.

4. The device according to claim 3, wherein the ledge is arranged in the holder such that a distance between the ledge and the at least one selected from the strainer and the filter is the same as or greater than the outer diameter of the glass ampule to be held by the holder.

5. The device according to claim 3, wherein the ledge is arranged in the holder such that a glass ampule to be held by the holder stands on the ledge such that the free end of the first lever lies above the ampule floor on the outer side of the deformable closed side wall.

6. The device according to claim 1, wherein, when the second lever is operated, the free end of the first lever presses onto the deformable closed side wall such that a vector of a force comprises a component which is oriented in a direction of the at least one selected from the strainer and the filter and/or which presses a glass ampule, to be held in the holder, into the holder in a direction of the ledge.

7. The device according to claim 1, wherein, on the free end of the first lever on a side facing towards the holder, a cutting edge is arranged.

8. The device according to claim 1, wherein the length ratio between the long lever arm and the short lever arm is at least 5 to 1.

9. The device according to claim 1, wherein a glass ampule is arranged in the holder and the glass ampule contains a monomer liquid for producing a medical bone cement, wherein the glass ampule, arranged in the holder, is the glass ampule that is manually openable in the device.

10. The device according to claim 1, wherein the second lever is rotatable in a plane in which the first lever is rotatable, wherein the movement of the second lever engages with the movement of the first lever.

11. The device according to claim 1, wherein the second axis of the second lever is arranged above the first axis of the first lever.

12. A medical cementing device for mixing a PMMA bone cement, the medical cementing device comprising:
    the device according to claim 1; and
    a cartridge with a mixing chamber containing a bone cement powder, wherein the mixing chamber is connected with the holder below the at least one selected from the strainer and the filter such that it is permeable to liquids.

13. The medical cementing device according to claim 12, further comprising:
    a glass ampule arranged in the holder and comprising a monomer liquid;
    a pump, with which the monomer liquid is to be pumped into the cartridge;
    a connection line, through which the monomer liquid is to be transported from the glass ampule into the cartridge;
    a manually operated stirring unit, with which the content of the cartridge can be mixed;
    a delivery piston which is provided in the cartridge such that it can be moved in the longitudinal direction and by which the mixed bone cement is to be discharged from the cartridge;
    a gas-permeable connection means in the delivery piston, which connects the interior chamber of the cartridge with the external environment; and
    a foot element which is connected to the holder, the cartridge and the levers, and with which the cementing device can be placed onto an even surface.

14. The cementing device according to claim 13, wherein the pump is a suction pressure pump, wherein a pressure pump element of the suction pressure pump is connected to the holder and the suction pump element of the suction pressure pump is connected to the mixing chamber of the cartridge.

15. A method comprising:
opening a glass ampule positioned within the device, according to claim 1, by manually rotating the long lever arm of the second lever around the second axis.

16. The method according to claim 15, wherein at least one selected from the glass ampule is inserted into the holder prior to the manual operation of the second lever and the glass ampule is inserted with an ampule floor of the glass ampule inserted first into the holder.

17. The method according to claim 15, wherein, following the opening of the glass ampule, a monomer liquid runs out of the glass ampule through the at least one selected from the strainer and the filter and is transported into a mixing chamber of the cartridge in which a bone cement powder is located, wherein subsequently, the bone cement powder and the monomer liquid are mixed in the mixing chamber of the cartridge.

18. The device according to claim 2, wherein the elastomer has a shore hardness of greater than 60 and the elastomer is a silicon rubber or an ethylene propylene diene rubber.

19. The medical cementing device according to claim 13, wherein the pump is a suction pressure pump, wherein the pressure pump element of the suction pressure pump is connected to the holder and the suction pump element of the suction pressure pump is connected to the mixing chamber of the cartridge via the gas-permeable connection means in the delivery piston.

20. A device for manually opening a glass ampule held within the device, the device comprising:
- a holder with side walls closed at least in sections, wherein the holder comprises at least one deformable closed side wall and a supporting element located opposite to the at least one deformable closed side wall;
- at least one selected from a strainer and a filter arranged below the holder;
- a first lever pivotable around a first axis such that the first lever rotates against the holder, wherein the first lever comprises a free end that is pressable against the deformable closed side wall of the holder; and
- a second lever pivotable around a second axis such that the second lever rotates against the holder, wherein the second axis divides the second lever into a short lever arm and a long lever arm,
wherein the free end of the first lever has a total thickness defined between a first side of the free end and an opposite second side of the free end, wherein the first side of free end faces the at least one deformable closed side wall of the holder and the opposite second side of the free end faces the short lever arm of the second lever, and the total thickness of the free end is disposed between the deformable closed side wall and short lever arm of the second lever.

\* \* \* \* \*